US010239828B2

(12) United States Patent
Rasmussen et al.

(10) Patent No.: US 10,239,828 B2
(45) Date of Patent: Mar. 26, 2019

(54) PROCESS FOR PREPARING GUANIDINO-FUNCTIONAL MONOMERS

(71) Applicant: 3M INNOVATIVE PROPERTIES COMPANY, St. Paul, MN (US)

(72) Inventors: Jerald K. Rasmussen, Woodville, WI (US); George W. Griesgraber, Eagan, MN (US); James I. Hembre, Plymouth, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 86 days.

(21) Appl. No.: 15/459,475

(22) Filed: Mar. 15, 2017

(65) Prior Publication Data
US 2017/0183299 A1 Jun. 29, 2017

Related U.S. Application Data

(62) Division of application No. 14/787,930, filed as application No. PCT/US2014/042028 on Jun. 12, 2014, now Pat. No. 9,670,149.

(60) Provisional application No. 61/835,669, filed on Jun. 17, 2013.

(51) Int. Cl.
| | |
|---|---|
| C07C 277/08 | (2006.01) |
| C07C 277/02 | (2006.01) |
| C07C 279/12 | (2006.01) |
| D06M 14/30 | (2006.01) |
| G01N 33/53 | (2006.01) |
| C08F 26/00 | (2006.01) |
| C08F 220/36 | (2006.01) |
| C09D 133/14 | (2006.01) |
| B01J 20/26 | (2006.01) |
| B01J 20/32 | (2006.01) |
| C08F 126/02 | (2006.01) |
| G01N 33/545 | (2006.01) |
| B01J 20/28 | (2006.01) |
| C08F 120/36 | (2006.01) |
| C09D 4/00 | (2006.01) |
| G01N 1/40 | (2006.01) |

(52) U.S. Cl.
CPC .......... *C07C 277/08* (2013.01); *B01J 20/261* (2013.01); *B01J 20/28033* (2013.01); *B01J 20/327* (2013.01); *C07C 277/02* (2013.01); *C07C 279/12* (2013.01); *C08F 26/00* (2013.01); *C08F 120/36* (2013.01); *C08F 126/02* (2013.01); *C08F 220/36* (2013.01); *C09D 4/00* (2013.01); *C09D 133/14* (2013.01); *D06M 14/30* (2013.01); *G01N 1/405* (2013.01); *G01N 33/53* (2013.01); *G01N 33/545* (2013.01)

(58) Field of Classification Search
None
See application file for complete search history.

(56) References Cited

U.S. PATENT DOCUMENTS

| | | | |
|---|---|---|---|
| 3,876,738 | A | 4/1975 | Marinaccio |
| 3,928,517 | A | 12/1975 | Knight |
| 4,260,628 | A | 4/1981 | Jonas |
| 4,539,256 | A | 9/1985 | Shipman |
| 4,707,265 | A | 11/1987 | Barnes, Jr. |
| 4,726,989 | A | 2/1988 | Mrozinski |
| 4,867,881 | A | 9/1989 | Kinzer |
| 5,120,594 | A | 6/1992 | Mrozinski |
| 5,260,360 | A | 11/1993 | Mrozinski |
| 5,458,782 | A | 10/1995 | Hou |
| 5,506,279 | A | 4/1996 | Babu |
| 5,962,544 | A | 10/1999 | Waller, Jr. |
| 6,056,529 | A | 5/2000 | Meyering |
| 6,267,916 | B1 | 7/2001 | Meyering |
| 6,413,070 | B1 | 7/2002 | Meyering |
| 6,776,940 | B2 | 8/2004 | Meyering |
| 7,125,603 | B2 | 10/2006 | David |

(Continued)

FOREIGN PATENT DOCUMENTS

| | | |
|---|---|---|
| CN | 1350022 | 5/2002 |
| JP | 47-40913 | 10/1972 |

(Continued)

OTHER PUBLICATIONS

Fletcher, et al., "Synthesis and pharmacological testing of polyaminoquinolines as blockers of the apamin-sensitive Ca2+-activated K+ channel (SKCa)," Bioorganic & Medicinal Chemistry, vol. 15, No. 16, Jun. 22, 2007, pp. 5457-5479.

Funhoff, et al., "Poly(3-guanidinopropyl methacrylate): A Novel Cationic Polymer for Gene Delivery," Bioconjugate Chem., 2004, vol. 15, pp. 1212-1220.

Hettinger, "Edeine III. The Composition of the Antibiotic Peptide Edeine B", Biochemistry, Dec. 1968, vol. 7, No. 12, pp. 4153-4160.

Katrizky et al., "Recent developments in guanylating agents," Arkivoc, 2005 (iv), pp. 48-97.

(Continued)

*Primary Examiner* — Satyanarayana R Gudibande
(74) *Attorney, Agent, or Firm* — Kent S. Kokko

(57) ABSTRACT

A process for preparing guanidino-functional, free radically polymerizable compounds comprises (a) combining (1) an amine compound comprising (i) at least one primary aliphatic amino group and (ii) at least one secondary aliphatic amino group, primary aromatic amino group, or secondary aromatic amino group, and (2) a guanylating agent; (b) allowing or inducing reaction of the amine compound and the guanylating agent to form a guanylated amine compound; (c) combining (1) the guanylated amine compound, and (2) a reactive monomer comprising (i) at least one ethylenically unsaturated group and (ii) at least one group that is reactive with an amino group; and (d) allowing or inducing reaction of the guanylated amine compound and the reactive monomer to form a guanidino-functional, free radically polymerizable compound.

18 Claims, No Drawings

(56) References Cited

U.S. PATENT DOCUMENTS

| | | | |
|---|---|---|---|
| 7,338,692 B2 | 3/2008 | Smith | |
| 8,586,338 B2 | 11/2013 | Etzel | |
| 8,652,582 B2 * | 2/2014 | Bothof | B01J 20/285 427/493 |
| 2012/0252091 A1 | 10/2012 | Rasmussen | |

FOREIGN PATENT DOCUMENTS

| WO | 2003-063797 | 8/2003 |
|---|---|---|
| WO | 2009-146321 | 12/2009 |
| WO | WO 2009-148869 | 12/2009 |
| WO | WO 2012-134636 | 10/2012 |
| WO | WO 2013-184366 | 12/2013 |
| WO | WO 2014-052215 | 4/2014 |

OTHER PUBLICATIONS

Lee, "Diamine and Triamine Analogs and Derivatives as Inhibitors of Deoxyhypusine Synthase: Synthesis and Biological Activity", Journal of Medicinal Chemistry, 1995, vol. 38, No. 16, pp. 3053-3061.
Wente, "Manufacture of Superfine Organic Fibers", Naval Research Laboratory, May 25, 1954, 23 pages.
Wente, "Superfine Thermoplastic Fibers", Industrial and Engineering Chemistry, Aug. 1956, vol. 48, No. 8, pp. 1342-1346.
International Search Report for PCT International Application No. PCT/US2014/042028, dated Oct. 14, 2014, 5 pages.
Supplementary European Search Report, EP Application No. 14814506, dated Dec. 19, 2016, 3 pages.

* cited by examiner

PROCESS FOR PREPARING GUANIDINO-FUNCTIONAL MONOMERS

STATEMENT OF PRIORITY

This application is a divisional of U.S. application Ser. No. 14/787,930, filed Oct. 29, 2015, which is a national stage filing under 35 U.S.C. 371 of PCT/US2014/042028, filed Jun. 12, 2014, which claims priority to U.S. Application No. 61/835,669, filed Jun. 17, 2013, the disclosure of which is incorporated by reference in its/their entirety herein.

TECHNICAL FIELD

This invention relates to processes for preparing guanidino-functional, free radically polymerizable compounds and, in another aspect, to certain compounds prepared thereby.

BACKGROUND

Detection, quantification, isolation, and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research.

Polymeric materials have been widely used for the separation and purification of various target biomaterials. Such separation and purification methods can be based on any of a number of binding factors or mechanisms including the presence of an ionic group, the size of the target biomaterial, a hydrophobic interaction, an affinity interaction, the formation of a covalent bond, and so forth.

For example, guanidino-functional polymers have been used to bind relatively neutral or negatively charged biomaterials such as viruses. Such polymers can be prepared from guanidino-functional monomers, but facile, industrially useful general methods for the preparation of such monomers (particularly monomers comprising aromatic substituents and N-substituted monomers) are currently lacking.

SUMMARY

Thus, we recognize that there is a need for improved processes for preparing guanidino-functional, free radically polymerizable compounds. Preferably, the processes will be facile, cost-effective, and/or efficient (for example, involving relatively few process steps). Ideally, the processes will provide relatively high yields of the guanidino-functional, free radically polymerizable compounds without requiring the isolation of intermediate compounds and/or the purification of final products.

Briefly, in one aspect, this invention provides a process for preparing guanidino-functional, free radically polymerizable compounds. The process comprises
 (a) combining
  (1) an amine compound comprising (i) at least one primary aliphatic amino group and (ii) at least one secondary aliphatic amino group, primary aromatic amino group, or secondary aromatic amino group, and
  (2) a guanylating agent;
 (b) allowing or inducing reaction of the amine compound and the guanylating agent to form a guanylated amine compound;
 (c) combining
  (1) the guanylated amine compound, and
  (2) a reactive monomer comprising (i) at least one ethylenically unsaturated group and (ii) at least one group that is reactive with an amino group; and
 (d) allowing or inducing reaction of the guanylated amine compound and the reactive monomer to form a guanidino-functional, free radically polymerizable compound.

Preferably, the amine compound comprises (i) only one or two primary aliphatic amino groups and (ii) only one secondary aliphatic amino group, primary aromatic amino group, or secondary aromatic amino group. The reactive monomer preferably comprises (i) at least one ethylenically unsaturated group and (ii) at least one isocyanato group. More preferably, the reactive monomer is a (meth)acryloyl-functional isocyanate.

It has been discovered that guanidino-functional, free radically polymerizable compounds can be readily prepared by a simple, essentially two-step process. The process utilizes starting amine compounds having at least one primary aliphatic amino group and at least one amino group that is less reactive than a primary aliphatic amino group (a secondary aliphatic amino group, primary aromatic amino group, or secondary aromatic amino group; hereinafter, a "less reactive amino group").

Surprisingly, such amine compounds can undergo rapid reaction with a guanylating agent almost exclusively through the primary aliphatic amino group(s), leaving the less reactive amino group(s) available for subsequent reaction with an ethylenically unsaturated compound. The less reactive amino group(s) generally can exhibit surprisingly good reactivity with the ethylenically unsaturated compound, even when the less reactive amino group is aromatic in nature (a primary or secondary aromatic amino group).

The process, due to its relatively high primary aliphatic amino group selectivity, can be carried out in a single vessel without the need for isolation of intermediate compounds (guanylated amines) resulting from reaction of the amine compound with the guanylating agent. Since guanylated amines are relatively polar and therefore relatively difficult to isolate from polar media, the ability to avoid their isolation can be quite advantageous.

The process of the invention can provide guanidino-functional, free radically polymerizable compounds in relatively high yield (for example, often yields of 90 percent or more, based upon nuclear magnetic resonance (NMR) analysis of the resulting product). Thus, in at least some embodiments, the process can meet the above-cited need for processes for preparing guanidino-functional monomers that will be facile, cost-effective, and/or efficient (for example, involving relatively few process steps), while ideally providing relatively high yields without requiring the isolation of intermediates.

The process of the invention can be used to prepare guanidino-functional monomers that can be free radically polymerized to provide guanidino-functional polymeric materials. The polymeric materials can be used for various different applications including the binding of relatively neutral or negatively charged biomaterials such as viruses and other microorganisms, proteins, cells, endotoxins, acidic carbohydrates, nucleic acids, and the like.

In another aspect, this invention also provides certain guanidino-functional, free radically polymerizable compounds that can be prepared by the process of the invention. The compounds include those represented by the following general formula

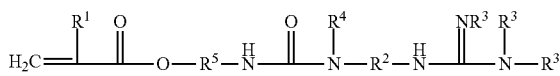

wherein
- $R^1$ is selected from hydrogen, alkyl, aryl, and combinations thereof;
- $R^2$ is selected from hydrocarbylene, heterohydrocarbylene, and combinations thereof;
- each $R^3$ is independently selected from hydrogen, hydrocarbyl, heterohydrocarbyl, and combinations thereof;
- $R^4$ is selected from hydrogen, hydrocarbyl, heterohydrocarbyl (for example, $R^4$ can comprise $-R^2-NH-C(=NR^3)-N(R^3)_2$, so as to provide a compound having more than one guanidino moiety), and combinations thereof;
- $R^5$ is selected from hydrocarbylene, heterohydrocarbylene, and combinations thereof;
- with the proviso that $R^2$ and/or $R^4$ comprise(s) at least one aromatic moiety (that is, $R^2$ comprises at least one aromatic moiety, $R^4$ comprises at least one aromatic moiety, or both $R^2$ and $R^4$ comprise at least one aromatic moiety).

In other aspects, this invention further provides a polymer comprising polymerized units of at least one compound of Formula I above, and an article comprising a substrate bearing the polymer. In yet another aspect, this invention also provides a method of capture or removal of a target biological species comprising (a) providing at least one article of the invention comprising at least one filter element; and (b) allowing a moving biological solution containing a target biological species to impinge upon the upstream surface of the filter element for a time sufficient to effect binding of the target biological species.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term and/or means one or all of the listed elements or a combination of any two or more of the listed elements.

The words preferred and preferably refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term comprises and variations thereof do not have a limiting meaning where these terms appear in the description and claims.

As used herein, a, an, the, at least one, and one or more are used interchangeably.

The above Summary of the Invention section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

Definitions

As used in this patent application:

"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);

"ethylenically unsaturated" means a monovalent group having a carbon-carbon double bond of formula $-CY=CH_2$ where Y is hydrogen, alkyl, cycloalkyl, or aryl;

"guanidino" means a monovalent group of formula $R_2N-C(=NR)NH-$ where each R is independently hydrogen, hydrocarbyl, heterohydrocarbyl, or a combination thereof, and where any two or more R groups optionally can be bonded together to form a ring structure (preferably, each R is independently hydrogen, alkyl, cycloalkyl, heteroalkyl, aryl, heteroaryl, or a combination thereof; more preferably, each R is independently hydrogen, alkyl, cycloalkyl, aryl, or a combination thereof);

"guanylating agent" means a compound that is reactive with an amino moiety of an amine compound to provide a guanidino-functional compound (for example, reaction of the guanylating agent with the amino moiety can form a guanidino moiety in situ through an addition reaction or a displacement reaction);

"isocyanato" means a monovalent group of formula $-N=C=O$;

"primary aliphatic amino" means a monovalent group of formula $-R'NH_2$ where R' is an aliphatic, alicyclic, heteroaliphatic, or heteroalicyclic moiety or a combination thereof;

"primary aromatic amino" means a monovalent group of formula $-ArNH_2$ where Ar is an aromatic or heteroaromatic moiety or a combination thereof;

"secondary aliphatic amino" means a monovalent group of formula $-R'NR''H$ where R' and R'' are independently selected from aliphatic, alicyclic, heteroaliphatic, and heteroalicyclic moieties and combinations thereof and "secondary aromatic amino" means a monovalent group of formula $-ArNR^hH$ or $-R^hNArH$ where Ar is an aromatic or heteroaromatic moiety and $R^h$ is an aromatic, aliphatic, alicyclic, heteroaromatic, heteroaliphatic, or heteroalicyclic moiety or a combination thereof.

Amine Compound

Amine compounds suitable for use in the process of the invention include those that comprise one or more (preferably, one or two) primary aliphatic amino groups and one or more (preferably, one or two) less reactive amino groups (that is, one or more groups selected from secondary aliphatic amino groups, primary aromatic amino groups, secondary aromatic amino groups, and combinations thereof). Preferably, the amine compounds comprise only one of the less reactive amino groups. More preferably, the amine compounds comprise only one or two primary aliphatic amino groups and only one of the less reactive amino groups. Most preferably, the amine compounds comprise only one primary aliphatic amino group and only one of the less reactive amino groups.

A class of suitable amine compounds includes those that can be represented by the following general formula

$$R^4NH-R^2-NH_2 \qquad (II)$$

wherein $R^4$ is selected from hydrogen, hydrocarbyl (preferably, alkyl, aryl, or a combination thereof), heterohydrocarbyl (preferably, heteroalkyl, heteroaryl, or a combination thereof; for example, containing one or more heteroatoms such as, for example, catenated oxygen, nitrogen, or sulfur heteroatoms; more preferably, heteroalkyl), and combinations thereof; $R^2$ is selected from hydrocarbylene (preferably, alkylene, arylene, or a combination thereof), heterohydrocarbylene (preferably, heteroalkylene, heteroarylene, or a combination thereof; for example, containing one or more heteroatoms such as, for example, catenated oxygen, nitrogen, or sulfur heteroatoms), and combinations thereof, and, optionally, $R^2$ can be bonded to $R^4$ to form a ring structure; with the proviso that when $R^4$ is hydrogen, $R^2$ is aralkylene or is a heterohydrocarbylene group comprising at least one secondary aliphatic amino group, primary aromatic amino group, or secondary aromatic amino group. Preferably, $R^4$ is hydrogen or hydrocarbyl (more preferably, hydrogen, alkyl, aralkyl, or aryl; even more preferably, hydrogen, alkyl having 1 to 12 carbon atoms, aralkyl having 7 to 12 carbon atoms, or aryl having 6 to 12 carbon atoms; most preferably, hydrogen, methyl, ethyl, isopropyl, benzyl, or phenyl). Preferably, $R^2$ is hydrocarbylene (more preferably, alkylene or aralkylene; even more preferably, alkylene having 1 to 20 carbon atoms or aralkylene having 7 to 22 carbon atoms; most preferably, ethylene, propylene, phenethylene, or benzylene). Preferably, $R^4$ is selected from hydrogen, hydrocarbyl, heterohydrocarbyl, and combinations thereof; and said $R^2$ is hydrocarbylene.

Representative examples of suitable amine compounds include N-methyl-1,2-ethanediamine, N-ethyl-1,2-ethanediamine, N-propyl-1,2-ethanediamine, N-isopropyl-1,2-ethanediamine, N-butyl-1,2-ethanediamine, N-benzyl-1,2-ethanediamine, N-phenyl-1,2-ethanediamine, N-hexadecyl-1,2-ethanediamine, N-(2-hydroxyethyl)-1,2-ethanediamine, N-methyl-1,3-propanediamine, N-isopropyl-1,3-propanediamine, N-myristyl-1,3-propanediamine, N-methyl-1,6-hexanediamine, diethylenetriamine, triethylenetetraamine, tetraethylenepentaamine, N-(2-aminoethyl)piperazine, dipropylenetriamine, bis(6-aminohexyl)amine, N-(2-picolyl)-1,3-propanediamine, N-(3-picolyl)-1,3-propanediamine, N-furfuryl-1,3-propanediamine, N-(2-phenylmercaptoethyl)-1,3-propanediamine, N-(2-phenoxyethyl)-1,3-propanediamine, 4-aminobenzylamine, 4-aminophenethylamine, 4-(N-methylamino)benzylamine, N-ethyl-(2-aminoethylthio)ethylamine, N-isopropyl-3,3'-oxy(bispropylamine), 3-(4-aminobenzamido)propylamine, and the like, and combinations thereof. Preferred amine compounds include N-methyl-1,2-ethanediamine, N-ethyl-1,2-ethanediamine, N-isopropyl-1,2-ethanediamine, N-butyl-1,2-ethanediamine, N-benzyl-1,2-ethanediamine, N-phenyl-1,2-ethanediamine, N-(2-hydroxyethyl)-1,2-ethanediamine, N-methyl-1,3-propanediamine, N-isopropyl-1,3-propanediamine, N-myristyl-1,3-propanediamine, N-methyl-1,6-hexanediamine, diethylenetriamine, triethylenetetraamine, N-(2-aminoethyl)piperazine, dipropylenetriamine, bis(6-aminohexyl)amine, N-(3-picolyl)-1,3-propanediamine, 4-aminobenzylamine, 4-aminophenethylamine, 4-(N-methylamino)benzylamine, and combinations thereof. Particularly preferred amine compounds include N-ethyl-1,2-ethanediamine, N-isopropyl-1,2-ethanediamine, N-benzyl-1,2-ethanediamine, N-phenyl-1,2-ethanediamine, N-(2-hydroxyethyl)-1,2-ethanediamine, N-methyl-1,3-propanediamine, 4-aminobenzylamine, 4-aminophenethylamine, diethylenetriamine, and combinations thereof.

Such amine compounds are generally commercially available or can be prepared by known methods. For example, a primary amine can be converted to an N-substituted-1,3-propanediamine by a sequence of cyanoethylation and reduction.

Guanylating Agent

Guanylating agents suitable for use in the process of the invention include compounds that are reactive with an amino moiety of an amine compound to provide a guanidino-functional compound. For example, reaction of the guanylating agent with an amino moiety of the amine compound can form a guanidino moiety in situ through an addition reaction or a displacement reaction.

The resulting guanidino-functional compound comprises a monovalent group of formula $R_2N-C(=NR)NH-$ where each R is independently hydrogen, hydrocarbyl, heterohydrocarbyl, or a combination thereof, and where any two or more R groups optionally can be bonded together to form a ring structure. Preferably, each R is independently hydrogen, alkyl (preferably, $C_1$-$C_4$ alkyl; more preferably, isopropyl), cycloalkyl (preferably, $C_3$-$C_7$ cycloalkyl; more preferably, cyclohexyl), heteroalkyl (preferably, $C_1$-$C_7$ heteroalkyl), aryl (preferably, $C_6$-$C_{12}$ aryl), heteroaryl (preferably, $C_2$-$C_{11}$ heteroaryl), or a combination thereof; more preferably, each R is independently hydrogen, alkyl, cycloalkyl, aryl, or a combination thereof; most preferably, each R is hydrogen.

The skilled artisan will recognize that the above formula represents the guanidino group as a free base with a localized C—N double bond. Depending upon the nature of the R substituents and the state of protonation/deprotonation of the group, however, other positional isomers of the C—N double bond can be possible. Thus, references herein to a guanidino group and/or to the above formula are intended to include all such positional isomers.

Suitable guanylating agents include O-alkylisourea salts, S-alkylisothiourea salts, carbodiimides, cyanamides, amidino-functional salts, and the like, and combinations thereof. Preferred guanylating agents include O-alkylisourea salts, carbodiimides, and combinations thereof.

Representative examples of suitable guanylating agents that can react with amines through displacement reactions include O-methylisourea sulfate (also known as O-methylisourea hemisulfate), O-methylisourea hydrogen sulfate, O-methylisourea acetate, O-ethylisourea hydrogen sulfate, O-ethylisourea hydrogen chloride, S-methylisothiourea sulfate (also known as S-methylisothiourea hemisulfate), S-methylisothiourea hydrogen sulfate, S-methylisothiourea acetate, S-ethylisothiourea hydrogen sulfate, S-ethylisothiourea hydrogen chloride, chloroformamidine hydrochloride, 1-amidino-1,2,4-triazole hydrochloride, 3,5-dimethylpyrazole-1-carboxamidine nitrate, pyrazole-1-carboxamidine hydrochloride, N-amidinopyrazole-1-carboxamidine hydrochloride, and the like, and combinations thereof. Representative examples of suitable guanylating agents that can react with amines through addition reactions include dicyclohexylcarbodiimide, N-ethyl-N'-(3-dimethylaminopropyl)carbodiimide, diisopropylcarbodiimide, diphenylcarbodiimide, cyanamide, and the like, and combinations thereof.

Preferred guanylating agents include O-methylisourea sulfate, O-methylisourea hydrogen sulfate, O-methylisourea acetate, O-ethylisourea hydrogen sulfate, O-ethylisourea hydrogen chloride, dicyclohexylcarbodiimide, N-ethyl-N'-(3-dimethylaminopropyl)carbodiimide, diisopropylcarbodiimide, diphenylcarbodiimide, and combinations thereof. Particularly preferred guanylating agents include O-methylisourea sulfate, O-methylisourea acetate, diisopropylcarbodiimide, and combinations thereof.

Such guanylating agents are known and can be prepared by known methods. At least some of the guanylating agents are also commercially available.

Reactive Monomer

Reactive monomers suitable for use in the process of the invention include compounds that comprise (i) at least one (preferably, only one) ethylenically unsaturated group and (ii) at least one (preferably, only one) group that is reactive with an amino group. Useful reactive monomers include ethylenically unsaturated isocyanates, ethylenically unsaturated acyl halides, and the like, and combinations thereof.

The reactive monomers are preferably (meth)acryloyl-functional. (As used herein, the term "(meth)acryloyl-functional" refers to acryloyl-functional and/or methacryloyl-functional; similarly, the term "(meth)acrylate" refers to an acrylate and/or a methacrylate). Preferred reactive monomers include ethylenically unsaturated isocyanates and combinations thereof (more preferably, (meth)acyloyl-functional isocyanates and combinations thereof).

Representative examples of suitable reactive monomers include 2-isocyanatoethyl (meth)acrylate, 3-isocyanatopropyl (meth)acrylate, 4-isocyanatocyclohexyl (meth)acrylate, 4-isocyanatostyrene, 3-isopropenyl-α,α-dimethylbenzylisocyanate, 2-methyl-2-propenoyl isocyanate, 4-(2-(meth)acryloyloxyethoxycarbonylamino) phenylisocyanate, allyl 2-isocyanatoethylether, 3-isocyanato-1-propene, (meth)acryloyl chloride, α-chloro(meth)acryloyl chloride, (meth)acryloyloxyacetyl chloride, 5-hexenoyl chloride, 2-(acryloyloxy)propionyl chloride, 3-(acryloylthioxy)propionoyl chloride, 3-(N-acryloyl-N-methylamino)propionoyl chloride, and the like, and combinations thereof. Preferred reactive monomers include 2-isocyanatoethyl (meth)acrylate, 3-isocyanatopropyl (meth)acrylate, 4-isocyanatocyclohexyl (meth)acrylate, 4-isocyanatostyrene, 2-methyl-2-propenoyl isocyanate, 3-isopropenyl-α,α-dimethylbenzylisocyanate, 4-(2-(meth)acryloyloxyethoxycarbonylamino) phenylisocyanate, allyl 2-isocyanatoethylether, 3-isocyanato-1-propene, and combinations thereof. Particularly preferred reactive monomers include 2-isocyanatoethyl acrylate and 2-isocyanatoethyl methacrylate, and combinations thereof.

Such reactive monomers can be prepared by known methods. At least some of the reactive monomers are also commercially available.

Process

The process of the invention can be carried out by first combining at least one amine compound and at least one guanylating agent (preferably, in at least one solvent in which the reactants can be substantially soluble). Generally, any order and manner of combination can be utilized, although it can sometimes be preferable to dissolve one reactant in solvent first (for example, the amine) prior to addition of the other reactant, or to dissolve each reactant separately in solvent prior to combination. Combination can be followed by allowing (for example, when using relatively highly reactive guanylating agents) or inducing (for example, by heating) reaction of the amine compound and the guanylating agent to form at least one guanylated amine compound.

The guanylated amine compound can be isolated and purified, if desired. Preferably, however, the process can be carried out without such isolation by combining the resulting reaction mixture with at least one reactive monomer and allowing or inducing (for example, by application of heat when using guanylated amine compounds of relatively low reactivity) reaction of the guanylated amine compound and the reactive monomer. If desired (for example, when using isocyanato-functional reactive monomer), this reaction can be carried out at a temperature below ambient (for example, a temperature below about 23° C., which can be achieved by, for example, cooling the reaction mixture in an ice bath prior to adding the reactive monomer) to minimize any side reactions (for example, reaction of the reactive monomer with water or other solvent).

Solvents that can be suitable for use in carrying out the process of the invention include those in which the reactants can be substantially soluble (generally, polar solvents). Such solvents include polar organic solvents (for example, dimethylsulfoxide (DMSO), dimethylformamide (DMF), acetonitrile, alkanols (for example, methanol, ethanol, isopropanol, 1-methoxy-2-propanol, and the like, and mixtures thereof), ketones (for example, acetone), N-methyl pyrrolidinone (NMP)), water (for example, deionized water), and the like, and mixtures thereof. Preferred solvents include water, alkanols, DMSO, DMF, acetone, and mixtures thereof (more preferably, water, alkanols, and mixtures thereof; most preferably, water).

Preferably, a stoichiometric amount or a relatively small stoichiometric excess (for example, an excess over the stoichiometric amount of about 5 mole percent or less) of guanylating agent and reactive monomer can be used, relative to the amounts of primary aliphatic amino groups and less reactive amino groups, respectively. Mechanical agitation or stirring can be used, if desired, to facilitate mixing. Optionally, heating can be used to facilitate dissolution and/or reaction (for example, this can be advantageous when using carbodiimide as the guanylating agent).

When using ethylenically unsaturated acyl halides as reactive monomer, base (for example, triethylamine or sodium hydroxide) can be added as an acid scavenger. Such base preferably can be added to the reaction mixture in neat form or as a solution in a suitable solvent, and/or the base preferably can be used in an amount from about 95 to about 105 mole percent, based on the total number of moles of acyl halide. When using carbodiimide as the guanylating agent, it can often be desirable to add one equivalent of an acid (for example, hydrochloric acid, acetic acid, sulfuric acid, or the like) to protonate the intermediate guanylated amine compound prior to reaction with the reactive monomer.

The resulting guanidino-functional, free radically polymerizable compounds can be isolated and/or purified, if desired, by using standard techniques such as decantation (for example, following precipitation optionally induced by cosolvent addition), filtration, rotary evaporation or freeze drying for solvent removal, and the like, and combinations thereof. The structure of the resulting product can be confirmed (and yield and/or purity determined) by nuclear magnetic resonance spectroscopy (NMR). In many cases, the resulting guanidino-functional, free radically polymerizable compounds are of such purity, however, that they do not need to be isolated and/or purified, but rather can be used in solution as prepared for conversion to guanidino-functional polymeric materials.

Polymerization and Use

The process of the invention can be used to prepare guanidino-functional monomers that can be free radically polymerized to provide guanidino-functional polymeric materials. The polymeric materials can be used for various different applications including the binding of relatively neutral or negatively charged biomaterials such as viruses and other microorganisms, acidic carbohydrates, proteins, nucleic acids, endotoxins, cells, and cell debris.

Polymerization of the guanidino-functional monomers can be carried out using known techniques. For example, the polymerization can be initiated with either a thermal initiator or a photoinitiator (preferably, a photoinitiator). Essentially any conventional free radical initiator can be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides (for example, tert-butyl hydroperoxide and cumene hydroperoxide), dicyclohexyl peroxydicarbonate, t-butyl perbenzoate; 2,2,-azo-bis(isobutyronitrile); and the like; and combinations thereof. Examples of commercially available thermal initiators include initiators available from DuPont Specialty Chemical (Wilmington, Del.) under the VAZO trade designation including VAZO™ 67 (2,2'-azo-bis(2-methylbutyronitrile)), VAZO™ 64 (2,2'-azo-bis(isobutyronitrile)), and VAZO™ 52 (2,2'-azo-bis(2,2-dimethylvaleronitrile)), as well as Lucidol™ 70 (benzoylperoxide) available from Elf Atochem North America, Philadelphia, Pa.

Useful photoinitiators include benzoin ethers such as benzoin methyl ether and benzoin isopropyl ether; substituted acetophenones such as 2, 2-dimethoxyacetophenone available as Irgacure™ 651 photoinitiator (Ciba Specialty Chemicals), 2,2 dimethoxy-2-phenyl-1-phenylethanone available as Esacure™ KB-1 photoinitiator (Sartomer Co.; West Chester, Pa.), 1-[4-(2-hydroxyethoxy)phenyl]-2-hydroxy-2-methyl-1-propan-1-one available as Irgacure™ 2959 (Ciba Specialty Chemicals), and dimethoxyhydroxyacetophenone; substituted $\alpha$-ketols such as 2-methyl-2-hydroxy propiophenone; aromatic sulfonyl chlorides such as 2-naphthalene-sulfonyl chloride; photoactive oximes such as 1-phenyl-1,2-propanedione-2-(O-ethoxy-carbonyl)oxime; and the like; and combinations thereof. Particularly preferred among these are the substituted acetophenones (especially 1-[4-(2-hydroxyethoxy)phenyl]-2-hydroxy-2-methyl-1-propan-1-one, Irgacure™ 2959, due to its water solubility). A particularly useful polymerizable photoinitiator is a 1:1 adduct of 2-vinyl-4,4-dimethylazlactone and Irgacure™ 2959, which can be prepared essentially as described in Example 1 of U.S. Pat. No. 5,506,279 (Babu et al.), the description of which preparation is incorporated herein by reference.

The initiator can be used in an amount effective to initiate free radical polymerization of the monomer(s). Such amount will vary depending upon, for example, the type of initiator and polymerization conditions utilized. The initiator generally can be used in amounts ranging from about 0.01 part by weight to about 5 parts by weight, based upon 100 parts total monomer.

The polymerization solvent can be essentially any polar solvent (for example, as described above). In many embodiments, the solvent can be water or a water/water-miscible organic solvent mixture. The ratio of water to organic solvent can vary widely, depending upon monomer solubility. With some monomers, the ratio typically can be greater than 1:1 (volume/volume) water to organic solvent (preferably, greater than 5:1; more preferably, greater than 7:1). With other monomers, a higher proportion of organic solvent (even up to 100 percent) can be preferred (with some alcohols especially).

Any such water-miscible organic solvent preferably has no groups that would retard polymerization. In some embodiments, the water-miscible solvents can be protic group-containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments, higher glycols such as poly(ethylene glycol) can be used. Specific examples include methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and the like, and combinations thereof.

In other embodiments, non-protic water-miscible organic solvents can be used. Such solvents include aliphatic esters (for example, methoxyethyl acetate, ethoxyethyl acetate, propoxyethyl acetate, butoxyethyl acetate, and triethyl phosphate), ketones (for example, acetone, methyl ethyl ketone, and methyl propyl ketone), and sulfoxides (for example, dimethyl sulfoxide).

The monomer concentration in the polymerization solvent can vary, depending upon a number of factors including, but not limited to, the nature of the monomer or monomers, the extent of polymerization desired, the reactivity of the monomer(s), and the solvent used. Typically, the monomer concentration can range from about 0.1 weight percent (wt %) to about 60 wt % (preferably, from about 1 wt % to about 40 wt %; more preferably, from about 5 wt % to about 30 wt %), based upon the total weight of monomer and solvent.

If desired, the polymerization can be carried out in the presence of a substrate, so as to form an article comprising a substrate bearing the resulting polymer. For example, an imbibing or coating solution comprising the monomer(s), any comonomer(s), initiator(s), and solvent(s) can be imbibed by or coated (or otherwise deposited) on a substrate. The substrate can be in essentially any form such as particles, fibers, films, or sheets. Suitable particles include, but are not limited to, organic particles, inorganic particles, and porous and nonporous particles. Preferably, the substrate is porous. Suitable porous substrates include, but are not limited to, porous particles, porous membranes, porous nonwoven webs, and porous fibers.

The substrate can be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate such as poly(ethylene)-co-poly(vinyl alcohol), poly(phosphazenes), poly(vinyl esters), poly(vinyl ethers), poly(vinyl alcohols), poly(carbonates), and the like, and combinations thereof.

In some embodiments, the thermoplastic polymer can be surface treated, such as by plasma discharge or by use of a primer, to provide suitable functionality to the surface of the substrate. Surface treatment can provide functional groups such as hydroxyl groups that can improve wetting by the monomer solution. One such useful plasma treatment is described in U.S. Pat. No. 7,125,603 (David et al.).

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene), poly(ethylene-co-1-butene-co-1-hexene), and the like, and combinations thereof.

Suitable fluorinated polymers include, but are not limited to, poly(vinyl fluoride), poly(vinylidene fluoride), copolymers of vinylidene fluoride (such as poly(vinylidene fluoride-co-hexafluoropropylene)), copolymers of chlorotrifluoroethylene (such as poly(ethylene-co-chlorotrifluoroethylene)), and the like, and combinations thereof.

Suitable polyamides include, but are not limited to, poly (iminoadipolyliminohexamethylene), poly(iminoadipolyliminodecamethylene), polycaprolactam, and the like, and combinations thereof. Suitable polyimides include, but are not limited to, poly(pyromellitimide), and the like, and combinations thereof.

Suitable poly(ether sulfones) include, but are not limited to, poly(diphenylether sulfone), poly(diphenylsulfone-co-diphenylene oxide sulfone), and the like, and combinations thereof.

Suitable copolymers of vinyl acetate include, but are not limited to, poly(ethylene-co-vinyl acetate), such copolymers in which at least some of the acetate groups have been hydrolyzed to afford various poly(vinyl alcohols), and the like, and combinations thereof.

A preferred substrate is a porous substrate that is a microporous membrane such as a thermally-induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Microporous membranes are further described in U.S. Pat. No. 4,529,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes comprise poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane comprising PVDF can be particularly desirable. TIPS membranes comprising PVDF are further described in U.S. Pat. No. 7,338,692 (Smith et al.).

In many embodiments, the substrate can have an average pore size that is typically greater than about 0.2 micrometers in order to minimize size exclusion separations, minimize diffusion constraints, and maximize surface area and separation based on binding of a target molecule. Generally, the pore size can be in the range of 0.1 to 10 micrometers (preferably, 0.5 to 3 micrometers; most preferably, 0.8 to 2 micrometers when used for binding of viruses and proteins). The efficiency of binding other target species can confer different optimal ranges.

In an exemplary embodiment, the porous substrate can comprise a nylon microporous film or sheet, such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. No. 3,928,517 (Knight et al.), U.S. Pat. No. 4,707,265 (Knight et al.), and U.S. Pat. No. 5,458,782 (Hou et al.).

In other embodiments, the porous substrate can be a nonwoven web, which can include nonwoven webs manufactured by any of the commonly known processes for producing nonwoven webs. As used herein, the term "nonwoven web" refers to a fabric that has a structure of individual fibers or filaments that are randomly and/or unidirectionally interlaid in a mat-like fashion.

For example, the fibrous nonwoven web can be made by wet laid, carded, air laid, spunlaced, spunbonding, or meltblowing techniques, or combinations thereof. Spunbonded fibers are typically small diameter fibers that are formed by extruding molten thermoplastic polymer as filaments from a plurality of fine, usually circular capillaries of a spinneret, with the diameter of the extruded fibers being rapidly reduced. Meltblown fibers are typically formed by extruding molten thermoplastic material through a plurality of fine, usually circular, die capillaries as molten threads or filaments into a high velocity, usually heated gas (for example, air) stream, which attenuates the filaments of molten thermoplastic material to reduce their diameter. Thereafter, the meltblown fibers are carried by the high velocity gas stream and are deposited on a collecting surface to form a web of randomly-dispersed, meltblown fibers. Any of the nonwoven webs can be made from a single type of fiber or from two or more fibers that differ in the type of thermoplastic polymer and/or thickness.

Further details of manufacturing methods of useful nonwoven webs have been described by Wente in "Superfine Thermoplastic Fibers," 48 Indus. Eng. Chem. 1342 (1956) and by Wente et al. in "Manufacture Of Superfine Organic Fibers," Naval Research Laboratories Report No. 4364 (1954).

Following polymerization, washing, and drying, typical total weight gains by the substrate generally can be in the range of about 5 percent (%) to about 30% (preferably, in the range of about 10% to about 25%; more preferably, in the range of about 12% to about 20%). Polymerization of the monomer(s) in the presence of a substrate can produce a polymer-bearing substrate. The polymer can be in the form of a coating or, in some embodiments, the polymer can be grafted (covalently bonded) to the surface of the substrate.

For example, the monomer(s) can be free radically polymerized and grafted to the surface of a substrate in the presence of a Type II photoinitiator, as described in International Patent Application No. US2013/042330 (3M Innovative Properties Co.), the description of which method is incorporated herein by reference. Alternatively, the monomer(s) can be free radically polymerized and grafted to a substrate comprising a crosslinked copolymer layer, the copolymer comprising photoinitiator-containing monomer units, as described in U.S. Provisional Patent Application No. 61/706,288 (Rasmussen et al.), the description of which method is incorporated herein by reference. In addition, the monomer(s) can be free radically polymerized and grafted to a substrate comprising a crosslinked polymer primer layer, as described in U.S. Patent Application Publication No. 2012/0252091 A1 (Rasmussen et al.), the description of which method is incorporated herein by reference.

The coated or grafted polymer can alter the original nature of the substrate. The resulting polymer-bearing substrates (functionalized substrates) can retain many of the advantages of the original substrate (for example, mechanical and thermal stability, porosity, and so forth) but can also exhibit enhanced affinity for biological species such as viruses, proteins, and the like. Porous substrates having a coating of guanidino-functional polymer can be particularly useful as filter media for the selective binding and removal of target biological species (including relatively neutral or negatively charged biomaterials such as viruses and other microorganisms, acidic carbohydrates, proteins, nucleic acids, endotoxins, bacteria, cells, cellular debris, and the like) from biological samples. Articles comprising the polymer-bearing substrates can further comprise conventional components such as housings, holders, adapters, and the like, and combinations thereof.

If desired, efficiency of binding and capture of biological species can be improved by using a plurality of stacked or layered, functionalized substrates (for example, functionalized porous membranes) as a filter element. Thus, a filter element can comprise one or more layers of functionalized substrate. The individual layers of the filter element can be the same or different. The layers can vary in porosity, degree of grafting, and so forth. The filter element can further comprise an upstream prefilter layer and/or a downstream support layer. The individual layers can be planar or pleated, as desired.

Examples of suitable prefilter and support layer materials include any suitable porous membranes of polypropylene, polyester, polyamide, resin-bonded or binder-free fibers (for example, glass fibers), and other synthetics (woven and non-woven fleece structures); sintered materials such as polyolefins, metals, and ceramics; yarns; special filter papers (for example, mixtures of fibers, cellulose, polyolefins, and binders); polymer membranes; and the like; and combinations thereof.

Useful articles for biological species capture or filtration applications include a filter cartridge comprising one or more of the above-described filter elements, a filter assembly comprising one or more of the above-described filter elements and a filter housing, and the like. The articles can be used in carrying out a method of capture or removal of a target biological species comprising (a) providing at least one article comprising at least one filter element; and (b) allowing a moving biological solution containing a target biological species to impinge upon the upstream surface of the filter element for a time sufficient to effect binding of the target biological species.

One class of guanidino-functional, free radically polymerizable compounds that can be prepared by the process of the invention can be represented by the following general formula

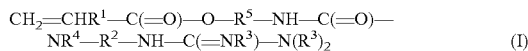

$$CH_2=CHR^1-C(=O)-O-R^5-NH-C(=O)-NR^4-R^2-NH-C(=NR^3)-N(R^3)_2 \quad (I)$$

wherein

R$^1$ is selected from hydrogen, alkyl, aryl, and combinations thereof (preferably, hydrogen or alkyl; more preferably, hydrogen or C$_1$-C$_4$ alkyl; even more preferably, hydrogen or methyl; most preferably, methyl);

R$^2$ is selected from hydrocarbylene, heterohydrocarbylene (for example, containing one or more heteroatoms such as, for example, catenated oxygen, nitrogen, or sulfur heteroatoms), and combinations thereof (preferably, hydrocarbylene; more preferably, alkylene or aralkylene; even more preferably, alkylene having 1 to 20 carbon atoms or aralkylene having 7 to 22 carbon atoms; most preferably, ethylene, propylene, phenethylene, or benzylene);

each R$^3$ is independently selected from hydrogen, hydrocarbyl, heterohydrocarbyl, and combinations thereof (preferably, hydrogen, alkyl, cycloalkyl, or heteroalkyl; more preferably, hydrogen, C$_1$-C$_4$ alkyl, C$_3$-C$_7$ cycloalkyl, or C$_1$-C$_7$ heteroalkyl; even more preferably, hydrogen, isopropyl, or cyclohexyl; most preferably, hydrogen);

R$^4$ is selected from hydrogen, hydrocarbyl, heterohydrocarbyl (for example, R$^4$ can comprise —R$^2$—NH—C(=NR$^3$)—N(R$^3$)$_2$, so as to provide a compound having more than one guanidino moiety (preferably, two)), and combinations thereof (preferably, hydrogen, hydrocarbyl, or guanidino-substituted alkyl; more preferably, hydrogen, alkyl, aralkyl, aryl, or guanidino-substituted alkyl; even more preferably, hydrogen, aralkyl, aryl, or guanidino-substituted alkyl; most preferably, hydrogen, benzyl, phenyl, or guanidino-substituted ethyl);

R$^5$ is selected from hydrocarbylene, heterohydrocarbylene (for example, containing one or more heteroatoms such as, for example, catenated oxygen, nitrogen, or sulfur heteroatoms), and combinations thereof (preferably, hydrocarbylene; more preferably, alkylene; even more preferably, alkylene having 1 to 20 carbon atoms; yet more preferably, propylene or ethylene; most preferably, ethylene);

with the proviso that R$^2$ and/or R$^4$ comprise(s) at least one aromatic moiety.

Such monomer(s) can be free radically polymerized to prepare a guanidino-functional polymer (comprising polymerized units of at least one compound of Formula I above) and/or an article comprising a substrate bearing the polymer (for example, an article comprising at least one filter element for use in biological species capture or filtration methods), as described above.

Preferred compounds of Formula I include those for which R$^1$ is hydrogen or methyl; R$^2$ is ethylene, propylene, phenethylene, or benzylene; R$^3$ is hydrogen, isopropyl, or cyclohexyl; R$^4$ is hydrogen, benzyl, phenyl, or guanidino-substituted ethyl; and R$^5$ is ethylene; with the proviso that either R$^2$ is phenethylene or benzylene, or R$^4$ is benzyl or phenyl, or both. More preferred compounds include 2-[[benzyl(2-guanidinoethyl)carbamoyl]amino]ethyl 2-methylprop-2-enoate, 2-[[2-guanidinoethyl(phenyl)carbamoyl]amino]ethyl 2-methylprop-2-enoate, 2-[[4-[[[N,N'-diisopropylcarbamimidoyl]amino]methyl]phenyl]carbamoylamino]ethyl 2-methylprop-2-enoate, 2-[[4-(2-guanidinoethyl)phenyl]carbamoylamino]ethyl prop-2-enoate, 2-[[ethyl(2-guanidinoethyl)carbamoyl]amino]ethyl 2-methylprop-2-enoate, 2-[[isopropyl(2-guanidinoethyl)carbamoyl]amino]ethyl 2-methylprop-2-enoate, 2-[[methyl(3-guanidinopropyl)carbamoyl]amino]ethyl 2-methylprop-2-enoate, and combinations thereof.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Sigma-Aldrich Chemical Company, St. Louis, Mo.

4-Aminobenzylamine was obtained from Sigma-Aldrich Chemical Company, St. Louis, Mo.

4-Aminophenethylamine was obtained from Sigma-Aldrich Chemical Company, St. Louis, Mo.

Barium acetate was obtained from MCB, Norwood, Ohio.

Diethylenetriamine was obtained from Sigma-Aldrich Chemical Company, St. Louis, Mo.

Diisopropylcarbodiimide was obtained from Sigma-Aldrich Chemical Company, St. Louis, Mo.

2-Isocanatoethyl acrylate (IEA) was obtained from Showa Denko KK, Kanagawa, Japan.

2-Isocyanatoethyl methacrylate (IEM) was obtained from Showa Denko KK, Kanagawa, Japan.

MBA refers to methylenebisacrylamide, available from Sigma-Aldrich Chemical Company, St. Louis, Mo.

N-(2-hydroxyethyl)-1,2-ethanediamine was obtained from Sigma-Aldrich Chemical Company, St. Louis, Mo.

O-methylisourea hemisulfate was obtained from Alfa Aesar, Ward Hill, Mass.

PEG(400)MA refers to polyethyleneglycol monomethacrylate, molecular weight (MW) about 400, obtained from Polysciences, Warrington, Pa.

S-BP refers to 4-(3-sulfopropyloxy)benzophenone, sodium salt (which is a water soluble benzophenone), prepared essentially as described in Japanese Patent No. 47040913 (Teijin Ltd.).

Test and Preparative Methods

Static Bovine Serum Albumin (BSA) Capacity Method for Functionalized Substrates

Functionalized substrates prepared as described in the Examples below were analyzed for their static BSA binding capacity by rocking one 24-mm diameter disk of the substrate to be analyzed in a solution of a test analyte overnight. The disk was prepared by die-punching a sheet of the substrate. Each disk was placed in a 5 mL centrifuge tube with 4.5 mL of BSA challenge solution (Catalog # A-7906, obtained from Sigma-Aldrich Chemical Company, St. Louis, Mo.) at a concentration of about 3.0 mg/mL in 25 millimolar tris(hydroxymethyl)aminomethane (TRIS) buffer (pH 8.0, obtained from Sigma-Aldrich Chemical Company, St. Louis, Mo.). The tubes were capped and tumbled overnight (typically 14 hours) on a rotating mixer (BARNSTEAD/THERMOLYN LABQUAKE™ Tube Shaker, obtained from VWR International, Eagan, Minn.). Then, the resulting supernatant solutions were analyzed using an ultraviolet-visible (UV-VIS) spectrometer (AGILENT™ 8453, Agilent Technologies, Santa Clara, Calif.) at 279 nanometers (nm) (with background correction applied at 325 nm). The static BSA binding capacity for each substrate was determined by comparison to the absorbance of the starting BSA solution, and results are reported in mg/mL as the average of three replicates.

Dynamic BSA Capacity Method for Functionalized Substrates

Functionalized substrates prepared as described in the Examples below were analyzed for dynamic binding of proteins by passing a solution of the test analyte through a 6-layer stack of each substrate. The stack was prepared by die-punching 25-mm diameter disks from a sheet of the substrate and stacking them. The stacks were placed in a 25 mm diameter holder attached to an AKTA™ chromatography system (obtained from GE Healthcare, Fairfield, Conn.). BSA was prepared at a concentration 1 mg/mL in 25 millimolar TRIS buffer containing 50 millimolar NaCl, pH 8.0. The BSA challenge solution was pumped through the substrate stack at a flow rate of 1 mL/min, and the ultraviolet (UV) absorbance of the resulting effluent was monitored at a wavelength of 280 nm. The dynamic BSA binding capacity of the substrate was determined using standard chromatography techniques and reported in mg/mL at 10 percent (%) breakthrough.

$^1$H NMR Analysis

Proton nuclear magnetic resonance ($^1$H NMR) analysis of the samples was carried out using a nuclear magnetic resonance (NMR) spectrometer (BRUKER™ A500, obtained from Bruker Corp., Billerica, Mass.) in solvents listed in each example or table entry.

Schematic Synthesis of Guanidino-Functional Amines and (Meth)Acrylate Derivatives Guanidino-functional amines and their methacrylate derivatives in Examples 1-6 and 8 were prepared in two steps as shown schematically below. Examples 7 and 9 were carried out in essentially the same manner, except that diisopropylcarbodiimide was used as the guanylating agent in Example 7, and isocyanatoethyl acrylate (IEA) was used as the reactive monomer in Example 9. For convenience, at least some of the resulting guanidino-functional monomers are named below as if in free base form but are understood to be in protonated form with a counterion derived from the guanylating agent used in their synthesis.

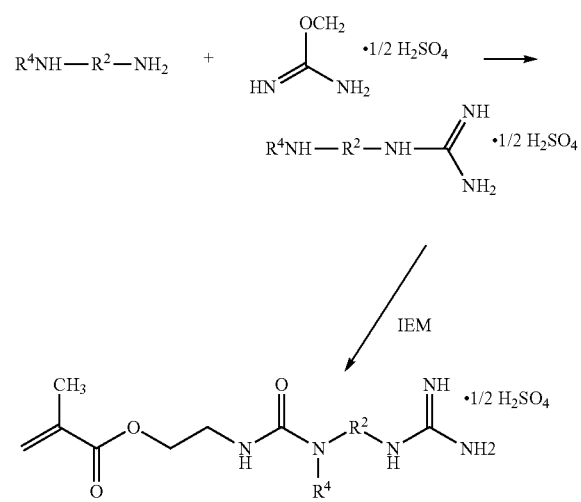

Example 1

Step 1: Synthesis of 2-[N-(2-hydroxyethyl)amino]ethylguanidine

N-(2-hydroxyethyl)-1,2-ethanediamine (10.4 grams, 0.1 mole) was dissolved in deionized (DI) water (50 mL) in a 250 mL round bottom flask with magnetic stirring. O-methylisourea hemisulfate (12.5 grams, 0.102 mole) was added to the flask as a solid. The resulting reaction mixture was stirred at ambient temperature (about 21° C.) for 4 hours to provide the desired guanylated amine product. The formation of the desired product was confirmed by NMR analysis ($^1$H-NMR (D$_2$O) δ 2.60 (t, 2H), 2.67 (t, 2H), 3.18 (t, 2H), 3.53 (t, 2H)).

Step 2: Reaction of 2-[N-(2-hydroxyethyl)amino]ethylguanidine with 2-Isocyanatoethyl Methacrylate (IEM)

The guanylated amine-containing reaction mixture was diluted with DI water (50 mL), and the flask was immersed in an ice-water bath and cooled to about 0° C. over 15 minutes. IEM (14.0 mL) was added to the flask by syringe. The resulting reaction mixture was allowed to stir and slowly warm up to room temperature (about 21° C.) over the course of 16 hours. The reaction mixture was filtered to remove a small amount of an insoluble byproduct (presumably the symmetrical urea derived from IEM). Formation of the desired adduct (guanidino-functional monomer, 2-[[2-guanidinoethyl(2-hydroxyethyl)carbamoyl]amino]ethyl 2-methylprop-2-enoate) was verified by NMR analysis ($^1$H-NMR (D$_2$O) δ 1.77 (s, 3H), 3.22 (m, 2H), 3.26 (m, 2H), 3.34 (m, 4H), 3.55 (m, 2H), 4.11 (m, 2H), 5.57 (s, 1H), 5.98 (s, 1H)).

Examples 2-6

Guanylated amines were synthesized in essentially the same manner as in Step 1 of Example 1, except that other starting primary, secondary diamines were converted to their respective guanidino-functional secondary amines. The formation of the desired guanylated amine products was confirmed by NMR analysis. Substituents R$^4$ and R$^2$ of the starting amines, the reaction times, and the NMR data for the resulting guanylated amine products are listed in Table 1 below.

TABLE 1

| Example No. | R$^4$ | R$^2$ | Reaction Time (hours) | Comments | NMR Data |
|---|---|---|---|---|---|
| 2 | Ethyl | (CH$_2$)$_2$ | 24 | None | $^1$H-NMR (D$_2$O) δ 0.93 (t, 3H), 2.49 (d, 2H), 2.65 (t, 2H), 3.18 (t, 2H) |
| 3 | Methyl | (CH$_2$)$_3$ | 24 | None | $^1$H-NMR (D$_2$O) δ 1.62 (t, 2H), 2.17 (s, 3H), 2.45 (t, 2H), 3.07 (t, 2H) |
| 4 | Benzyl | (CH$_2$)$_2$ | 24 | None | $^1$H-NMR (D$_2$O) δ 2.63 (t, 2H), 3.15 (t, 2H), 3.61 (s, 2H), 7.22 (m, 3H), 7.27 (m, 2H) |
| 5 | Isopropyl | (CH$_2$)$_2$ | 7.5 | None | $^1$H-NMR (D$_2$O) δ 0.90 (d, 6H), 2.65 (t, 2H), 2.71 (septet, 1H), 3.16 (t, 2H) |
| 6 | Phenyl | (CH$_2$)$_2$ | 18 | Phase Separated | $^1$H-NMR (CD$_3$OD) δ 3.32 (m, 4H), 6.66 (t, 1H), 6.68 (d, 2H), 7.10 (d, 2H) |

The resulting guanylated amines were reacted with IEM in essentially the same manner as described in Step 2 of Example 1 to produce their corresponding methacrylate derivatives. The formation of the desired products (guanidino-functional monomers) was confirmed by NMR analysis. The reaction times used, as well as the NMR data for the resulting products, are listed in Table 2 below.

TABLE 2

| Example No. | Reaction Time (hours) | Comments | NMR Data |
|---|---|---|---|
| 2 | 1 | None | $^1$H-NMR (D$_2$O) δ 0.95 (t, 3H), 1.77 (s, 3H), 3.11 (q, 2H), 3.20 (m, 2H), 3.30 and 3.34 (2 m, 4H), 4.12 (m, 2H), 5.58 (s, 1H), 5.98 (s, 1H) |
| 3 | 1 | None | $^1$H-NMR (D$_2$O) δ 1.65 (t, 2H), 1.77 (s, 3H), 2.72 (s, 3H), 3.01 (t, 2H), 3.19 (3, 2H), 3.34 (t, 2H), 4.11 (t, 2H), 5.58 (s, 1H), 5.98 (s, 1H) |
| 4 | 6 | Product Precipitated, Filtered | $^1$H-NMR (CD$_3$OD) δ 1.87 (s, 3H), 3.25 (t, 2H), 3.39 (t, 2H), 3.47 (t, 2H), 4.19 (t, 2H), 4.52 (s, 2H), 5.57 (s, 1H), 6.05 (s, 1H), 7.21 (m, 3H), 7.28 (m, 2H) |
| 5 | 15 | None | $^1$H-NMR (D$_2$O) δ 0.99 (d, 6H), 1.77 (s, 3H), 3.17 (m, 4H), 3.36 (t, 2H), 3.80 (septet, 1H), 4.14 (t, 2H), 5.58 (s, 1H), 5.98 (s, 1H) |
| 6 | 0.5 | Diluted with Methanol Instead of Water | $^1$H-NMR (D$_2$O) δ 1.89 (s, 3H), 3.33 (t, 2H), 3.38 (t, 2H) 3.75 (t, 2H)4.15 (t, 2H) 5.60 (s, 1H), 6.04 (s, 1H), 7.25 (d, 2H), 7.35 (t, 1H), 7.45 (d, 2H) |

Example No. 2: 2-[[ethyl(2-guanidinoethyl)carbamoyl]amino]ethyl 2-methylprop-2-enoate
Example No. 3: 2-[[3-guanidinopropyl(methyl)carbamoyl]amino]ethyl 2-methylprop-2-enoate
Example No. 4: 2-[[benzyl(2-guanidinoethyl)carbamoyl]amino]ethyl 2-methylprop-2-enoate
Example No. 5: 2-[[2-guanidinoethyl(2-propyl)carbamoyl]amino]ethyl 2-methylprop-2-enoate
Example No. 6: 2-[[2-guanidinoethyl(phenyl)carbamoyl]amino]ethyl 2-methylprop-2-enoate Polymerization and Grafting of Guanidino-Functional Monomers of Examples 1-6 and Testing of Resulting Functionalized Substrates Coating solutions were prepared by mixing 5.0 grams of guanidino-functional monomer solution prepared as described in Examples 1-6 with S-BP (250 μL of a 0.1 gram/mL solution in DI water). As shown in Table 3 below, some of, the aqueous monomer solutions were lyophilized and reconstituted up to 5.0 grams with methanol, or a 1:1 by weight mixture of water and methanol, as solvent. In some cases, MBA (0.1 g), PEG(400)MA (0.4 g), or both MBA (0.1 g) and PEG(400)MA (0.4 g) were added to the coating solution, as shown in Table 3.

For each coating solution, a 9 cm×12 cm piece of nylon 66 membrane (single reinforced layer nylon three-zone membrane, nominal pore size 1.8 μm, #080ZN obtained from 3M Purification, Inc., Meridan, Conn.) was placed on a piece of polyester film, and approximately 4.5 mL of coating solution was pipetted onto the top surface of the membrane. The coating solution was allowed to soak into the membrane for about 1 minute, and then a second piece of polyester film was placed on top of the membrane. Excess coating solution was removed by rolling a 2.28 kg weight over the top of the resulting three layer sandwich, and the sandwich was irradiated using a UV stand (obtained from Classic Manufacturing, Inc., Oakdale, Minn.) equipped with 18 bulbs (Sylvania RG2 40W F40/350BL/ECO, 10 above and 8 below the substrate, 1.17 meter long, spaced 5.1 cm on center), with an irradiation time of 15 minutes. The top and bottom polyester sheets were removed, and the resulting grafted membrane (a functionalized substrate) was placed in a 250 mL polyethylene bottle. The bottle was filled with DI water, sealed, and shaken for 30 minutes to wash off any residual monomer or ungrafted polymer. The water was replaced with 0.9% saline, and the functionalized substrate was washed for 30 minutes twice with fresh saline solution, then final washed for 30 minutes with DI water and allowed to dry.

The functionalized substrates were tested for BSA binding capacities. The compositions of the coating solutions, as well as the BSA binding capacities of the resulting functionalized substrates are shown in Table 3 below.

TABLE 3

| Example No. | Solvent | MBA | PEG(400)MA | BSA Capacity (mg/mL) | |
|---|---|---|---|---|---|
| | | | | Static | Dynamic |
| 1 | Water | None | None | 55 | Not Tested |
| 1 | Water | None | Yes | 71 | Not Tested |
| 2 | Water | None | None | 56 | Not Tested |
| 2 | Methanol | None | None | 79 | Not Tested |
| 2 | Methanol | None | Yes | 106 | Not Tested |
| 3 | Water | None | None | 53 | Not Tested |
| 3 | Methanol | None | None | 103 | Not Tested |
| 3 | Methanol | None | Yes | 128 | 78 |
| 4 | Water | None | None | 99 | Not Tested |
| 4 | Water | Yes | None | 104 | Not Tested |
| 4 | Water | None | Yes | 116 | Not Tested |
| 4 | Water | Yes | Yes | 102 | 63 |
| 5 | Water | None | None | 60 | Not Tested |
| 5 | Methanol | None | None | 47 | Not Tested |
| 5 | Methanol | None | Yes | 86 | Not Tested |
| 6 | Methanol/ Water (1:1 w/w) | None | None | 69 | Not Tested |

Another coating solution was prepared from 5.0 grams of the methanolic monomer solution of Example 3 by adding S-BP (250 µL of a 0.1 gram/mL solution in DI water) and diluting with methanol (1.7 grams). This coating solution was used to graft a nylon membrane essentially as described above. When tested, the resulting functionalized substrate exhibited a static BSA capacity of 129 mg/mL and a dynamic BSA capacity of 102 mg/mL.

Example 7

Step 1: Preparation of N-(4-aminobenzyl)-N',N''-diisopropylguanidine

4-Aminobenzylamine (1.22 grams, 10 mmole) and diisopropylcarbodiimide (1.26 grams, 10 mmole) were weighed into a 6 dram glass vial. The vial was sealed and placed on a rocker at room temperature (about 21° C.) for 18 hours. NMR analysis indicated about 87% conversion to guanylated amine product. The reaction mixture was placed in an oven at 60° C. for 4 hours to complete conversion to the expected product. Formation of the desired guanylated amine product was confirmed with NMR analysis ($^1$H-NMR (CD$_3$OD): δ 1.16 (d, 12H), 3.77 (septet, 2H), 4.28 (s, 2H), 6.70 (d, 2H), 7.03 (d, 2H)).

Step 2: Reaction of N-(4-aminobenzyl)-N',N''-diisopropylguanidine with 2-Isocyanatoethyl Methacrylate (IEM)

The guanylated amine product (that is, N-(4-aminobenzyl)-N',N''-diisopropylguanidine) was dissolved in DI water (5.0 grams) and methanol (4.0 grams), and concentrated hydrochloric acid (0.82 mL) was added to the resulting solution to protonate the guanidino moiety of the guanylated amine. IEM (1.50 grams) was added to the solution, the vial was sealed, and the sealed vial was placed on a rocker at room temperature (about 21° C.) for 18 hours to provide the desired guanidino-functional monomer product, 2-[[4-[[[N, N'-diisopropylcarbamimidoyl]amino]methyl]phenyl]carbamoylamino]ethyl 2-methylprop-2-enoate. NMR analysis confirmed the formation of the desired product ($^1$H-NMR (CD$_3$OD): δ 1.19 (d, 12H), 1.92 (s, 3H), 3.49 (t, 2H), 3.85 (septet, 2H), 4.20 (t, 2H), 4.44 (s, 2H), 5.61 (s, 1H), 6.14 (s, 1H), 7.21 (d, 2H), 7.40 (d, 2H)).

Example 8

Step 1a: Preparation of Bis(2-guanidinoethyl)amine, Sulfuric Acid Salt

Diethylenetriamine (5.15 grams, 0.05 mole) was dissolved in DI water (25 mL) in a 100 mL round bottom flask with magnetic stirring. O-Methylisourea hemisulfate (12.5 grams, 0.102 mole) was added to the flask as a solid. The resulting reaction mixture was stirred at ambient temperature (about 21° C.) for 18 hours, at which time the reaction mixture had solidified. The reaction mixture was diluted with deionized water, filtered, washed with additional water, and allowed to dry. The yield was 13.05 g (91.6%), and the formation of the desired guanylated amine product was confirmed with NMR analysis ($^1$H-NMR (D$_2$O plus 1 drop concentrated hydrochloric acid) δ 3.16 (br. t, 4H), 3.44 (br. t, 4H)).

Step 1b: Preparation of Bis(2-guanidinoethyl)amine, Bis Acetic Acid Salt

A solution of O-methylisourea hemisulfate (29.52 grams, 0.24 equivalents) was prepared in deionized water (60 mL) in a 500 mL round bottom flask equipped with overhead stirring. A separate solution of barium acetate (30.65 grams) in deionized water (60 mL) was added to the stirring solution in the flask. The resulting mixture was stirred at ambient temperature (about 21° C.) for about 10 minutes and was then poured into four 50-mL polypropylene centrifuge tubes and centrifuged at a setting of 3000 relative centrifugal force (rcf) for 10 minutes to separate out precipitated barium sulfate. The resulting supernatant solution was poured into a 500 mL round bottom flask to provide a total of 90.0 grams of O-methylisourea acetate solution. The solution was magnetically stirred, and diethylenetriamine (7.65 grams, 74 mmole) was added to the solution. After 2.5 hours reaction time, NMR analysis indicated complete conversion to the desired bis-guanidine salt ($^1$H-NMR (D$_2$O) δ 1.74 (s, 6H), 2.63 (t, 4H), 3.14 (t, 4H)).

Step 2: Reaction of Bis(2-guanidinoethyl)amine, Bis Acetic Acid Salt, with 2-Isocyanatoethyl Methacrylate (IEM)

The mixture comprising the bis-guanidine salt (that is, bis(2-guanidinoethyl)amine, bis acetic acid salt) was diluted with DI water (74.25 mL), the reaction flask was cooled in an ice-bath for 15 minutes, and IEM (11.47 grams) was added to the flask. The resulting mixture was stirred overnight, and a small amount of colorless precipitate was filtered off. NMR analysis of the resulting filtrate indicated conversion to the desired bis-guanidine monomer, 2-[[bis (2-guanidinoethyl)carbamoyl]amino]ethyl 2-methylprop-2-enoate, bis acetic acid salt ($^1$H-NMR (D$_2$O) δ 1.77 (s, 6H), 3.21 (t, 6H), 3.33 (m, 4H), 4.11 (t, 2H), 5.59 (s, 1H), 5.99 (s, 1H)).

Example 9

Step 1: Preparation of 4-Aminophenethylguanidine

4-Aminophenethylamine (3.4 grams, 2.5 mmole) was dissolved in deionized water (25 mL) in a 100 mL round bottom flask with magnetic stirring. O-Methylisourea hemisulfate (3.14 grams, 2.55 mmole) was added to the flask as a solid. The resulting reaction mixture was stirred at ambient temperature (about 21° C.) for 24 hours to give the desired guanylated amine product, which was confirmed by NMR analysis ($^1$H-NMR (CD$_3$OD) δ 2.76 (t, 2H), 3.33 (t, 2H), 6.71 (d, 2H), 7.03 (d, 2H)).

Step 2: Reaction of 4-Aminophenethylguanidine with 2-Isocanatoethyl Acrylate (IEA)

The guanylated amine-containing reaction mixture was stirred and cooled in an ice-water bath for 30 minutes, then 2-isocyanatoethyl acrylate (3.53 grams, 2.5 mmole) was added to the reaction mixture by syringe. A product rapidly separated out as a gummy solid. Methanol (25 mL) was added to the resulting mixture to dissolve the solid. After 2 hours, NMR analysis indicated complete conversion to the desired guanidino-functional monomer product, 2-[[4-(2-guanidinoethyl)phenyl]carbamoylamino]ethyl prop-2-enoate ($^1$H-NMR (CD$_3$OD) δ 2.78 (t, 2H), 3.30 (t, 2H), 3.48 (t, 2H), 4.22 (t, 2H), 5.90 (dd, 1H), 6.18 (dd, 1H), 6.42 (dd, 1H), 7.10 (d, 2H), 7.31 (d, 2H)).

Example 10

The resulting monomer solution of Example 7 was diluted with methanol (10 grams). 2,2'-Azobis(2-amidinopropionamidine) dihydrochloride (0.04 grams) was added to the diluted solution, and the resulting solution was then purged by bubbling nitrogen gas through the solution for 10 minutes. The vial containing the purged solution was sealed and placed in a hot water bath at 60° C. for three hours to provide a soft, rubbery, hydrogel-like polymer.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:

1. A guanidino-functional, free radically polymerizable compound represented by the following general formula I $$H_2C=\overset{R^1}{\underset{}{C}}-\overset{O}{\underset{}{C}}-O-R^5-\overset{H}{\underset{}{N}}-\overset{O}{\underset{}{C}}-\overset{R^4}{\underset{}{N}}-R^2-\overset{H}{\underset{}{N}}-\overset{NR^3}{\underset{}{C}}-N-R^3 \qquad I$$

wherein
R$^1$ is selected from hydrogen, alkyl, aryl, and combinations thereof;
R$^2$ is selected from hydrocarbylene, heterohydrocarbylene, and combinations thereof;
each R$^3$ is independently selected from hydrogen, hydrocarbyl, heterohydrocarbyl, and combinations thereof;
R$^4$ is selected from hydrogen, hydrocarbyl, heterohydrocarbyl, and combinations thereof;
R$^5$ is selected from hydrocarbylene, heterohydrocarbylene, and combinations thereof;
with the proviso that R$^2$ and/or R$^4$ comprise(s) at least one aromatic moiety.

2. A polymer comprising polymerized units of at least one compound of claim 1.

3. An article comprising a substrate bearing the polymer of claim 2.

4. The article of claim 3, wherein the substrate is a microporous membrane.

5. The article of claim 3, wherein the polymer is grafted to the substrate.

6. The article of claim 3, wherein said article comprises at least one filter element.

7. The compound of claim 1, wherein R$^1$ is hydrogen or methyl.

8. The compound of claim 1, wherein R$^2$ is alkylene or aralkylene.

9. The compound of claim 8, wherein R$^2$ is ethylene, propylene, phenethylene, or benzylene.

10. The compound of claim 1, wherein R$^3$ is independently selected from hydrogen, isopropyl, or cyclohexyl.

11. The compound of claim 10, wherein R$^3$ is hydrogen.

12. The compound of claim 1, wherein R$^4$ is hydrogen, alkyl, aralkyl, aryl, or guanidino-substituted alkyl and combinations thereof.

13. The compound of claim 12, wherein R$^4$ is aralkyl or aryl.

14. The compound of claim 12, wherein R$^4$ is hydrogen, alkyl, aralkyl, aryl, or —R$^2$—NH—C(=NR$^3$)—N(R$^3$)$_2$ and combinations thereof.

15. The compound of claim 1, wherein R$^3$ is hydrogen, and R$^4$ is hydrogen, alkyl, aralkyl, aryl, or —R$^2$—NH—C(=NR$^3$)—N(R$^3$)$_2$ and combinations thereof.

16. The compound of claim 1, wherein R$^5$ is propylene or ethylene.

17. The compound of claim 1, wherein R$^3$ is hydrogen, and R$^4$ is benzyl or phenyl.

18. The compound of claim 1, wherein R$^1$ is hydrogen or alkyl, R$^2$ is alkylene, R$^3$ is hydrogen, and R$^4$ is benzyl or phenyl.

* * * * *